(12) United States Patent
Kosaka

(10) Patent No.: US 7,820,449 B2
(45) Date of Patent: Oct. 26, 2010

(54) TEST STRIP FOR CREATININE DETERMINATION

(75) Inventor: Hideko Kosaka, Kyoto (JP)

(73) Assignee: ARKRAY, Inc., Kyoto (JP)

( * ) Notice: Subject to any disclaimer, the term of this patent is extended or adjusted under 35 U.S.C. 154(b) by 637 days.

(21) Appl. No.: 10/530,790

(22) PCT Filed: Oct. 15, 2003

(86) PCT No.: PCT/JP03/13166
§ 371 (c)(1),
(2), (4) Date: Apr. 8, 2005

(87) PCT Pub. No.: WO2004/036225
PCT Pub. Date: Apr. 29, 2004

(65) Prior Publication Data
US 2005/0266574 A1    Dec. 1, 2005

(30) Foreign Application Priority Data
Oct. 15, 2002    (JP) .............................. 2002-300959

(51) Int. Cl.
*G01N 33/00* (2006.01)

(52) U.S. Cl. .............................. 436/98; 422/56; 422/57; 422/58; 436/169; 435/287.9

(58) Field of Classification Search .................. 422/56, 422/57, 58; 435/287.9; 436/98, 169
See application file for complete search history.

(56) References Cited

U.S. PATENT DOCUMENTS 4,275,031 A * 6/1981 Fischer et al. .................. 422/57

(Continued)

FOREIGN PATENT DOCUMENTS

DE    3602999 A1 *    8/1986

(Continued)

OTHER PUBLICATIONS

Itsuo Mori, "Spectrophotometric Determination of Creatinine using o-Hydroxy-hydroquinonephthalein-Palladium (II) Complex", 1983, Chem. Pharm. Bull. 31 (4), p. 1389-1391.*

(Continued)

*Primary Examiner*—Lyle A Alexander
*Assistant Examiner*—Dennis M White
(74) *Attorney, Agent, or Firm*—Hamre, Schumann, Mueller & Larson, P.C.

(57) ABSTRACT

The present invention provides a novel test piece for creatinine measurement. The test piece includes a compound expressed by the following formula (1), a metal that forms a colored complex with the compound, and a buffer agent in a porous material. The amount of creatinine is determined by optically measuring a colored complex of the compound and the metal and evaluating the degree of inhibition of the colored complex formation by creatinine. In the formula (1), $R^1$ represents H, $SO_3X$, or COOX. $R^4$ and $R^6$ represent OH, $SO_3X$, or COOX and may be either the same or different. $R^2$, $R^3$, $R^5$, and $R^7$ represent H, OH, Cl, Br, I, $NO_2$, NO, or $CH_3$ and may be either the same or different. Xs in the $R^1$, $R^4$, and $R^6$ represent H, Na, K, or $NH_4$ and may be either the same or different.

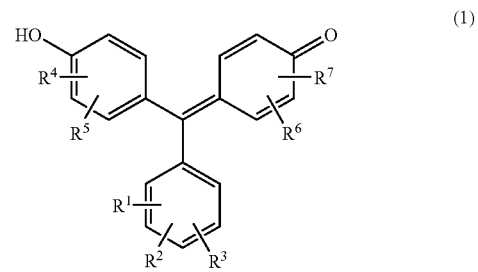

(1)

12 Claims, 1 Drawing Sheet

U.S. PATENT DOCUMENTS

| | | | |
|---|---|---|---|
| 4,960,710 A * | 10/1990 | Lau | 436/86 |
| 5,151,370 A | 9/1992 | Denney | |
| 5,374,561 A * | 12/1994 | Pugia | 436/98 |
| 5,399,498 A | 3/1995 | Pugia | |
| 5,464,777 A | 11/1995 | Yip | |
| 2002/0037591 A1 * | 3/2002 | Kosaka | 436/166 |

FOREIGN PATENT DOCUMENTS

| | | |
|---|---|---|
| EP | 0 952 451 | 10/1999 |
| JP | 7-209304 | 8/1995 |
| JP | 8-105899 | 4/1996 |

OTHER PUBLICATIONS

Roy W. Bonsnes et al., "On the Colorimetric Determination of Creatinine by the Jaffe Reaction", Journal of Biological Chemistry, 1945, 158, pp. 581-591.

Stanley R. Benedict et al., "Some Applications of a New Color Reaction for Creatinine", Journal of Biological Chemistry, 1936, 113, p. 515-532.

Enzo Tanganelli et al., "Enzymic Assay of Creatinine in Serum and Urine with Creatinine Lminohydrolase and Glutamate Dehydrogenase", Clinical Chemistry, 1982, 28, p. 1461-1464.

Yang, Dingguo, "Study on chromogenic reaction of palladium (II) with Chrome Azurol B-cetyldimethylammonium acetate-Triton X-100 and its application", Chemical Abstracts Service, 1990, XP002490393.

Yang, at al., "Spectrophotometric study on the color reaction of complex of palladium with Chrome Azurol B and cetyltrimethylammonium bromide", Chemical Abstracts Service, 1988, XP02490394.

Duchkova, et al., "Spectrophotmetric determination of the platinum metals. Determination of palladium with Eriochrome Cyanine R in the presence of cetylpyridinium bromide", Chemical Abstracts Service, 1976. XP002490395.

Egermaierova, et al., "Spectrophotometric determination of platinum metals. VII. Determination of palladium with bromopyrogallol red and pyrocatechol violet", Chemical Abstract Service, 1983, XP002490396.

Mori, et al.. "Spectrophotometric Determination of Creatinine using o-Hydroxy-hydroquinonephthalein-Palladium (iII) Complex", Chem. Pharm. Bull. 31 (4) 1389-1391, 1983, XP009104072.

* cited by examiner

TEST STRIP FOR CREATININE DETERMINATION

TECHNICAL FIELD

The present invention relates to a test piece for creatinine measurement.

BACKGROUND ART

The measurement of creatinine has been performed in the field of clinical care because creatinine is useful as an indicator of kidney function.

Creatinine can be measured generally by a chemical or enzymatic method. Examples of the chemical method include a Jaffe method (see, e.g., Bonsnes and Taussky, Journal of Biological Chemistry, 1945, 158, p. 581) and a Benedict-Behre method (see, e.g., Benedict and Behre, Journal of Biological Chemistry, 1936, 113, p. 515). When creatinine reacts with picric acid under alkaline conditions, it changes color to orange-red. The Jaffe method utilizes this property of creatinine, and the Benedict-Behre method uses 3,5-dinitrobenzoic acid instead of the picric acid. Examples of the enzymatic method include a creatinine deaminase method and a creatinine amidohydrolase (creatininase) method (see, e.g., Tanganelli et al., Clinical Chemistry, 1982, 28, p. 1461). In the creatinine deaminase method, an enzyme acts on creatinine to produce ammonia, and the ammonia is measured calorimetrically. In the creatinine amidohydrolase method, creatinine is converted into creatine using creatininase, and the creatine is treated with sarcosine oxidase or peroxidase and then is measured calorimetrically.

DISCLOSURE OF INVENTION

The Jaffe and Benedict methods involve a chemical condensation reaction, and the cost of reagents to be used is very low. However, this reaction does not occur easily if the reaction temperature is not raised, e.g., to 35° C. or more, and thus requires a high temperature and long time (e.g., 10 minutes or more). Moreover, a strong alkaline reagent is used to cause a reaction under strong alkaline conditions (with a pH of 11 or more). Accordingly, a special apparatus or jig is necessary for measurement, and a liquid waste treatment after the measurement is a serious problem.

On the other hand, the enzymatic method allows a reaction to progress under temperate conditions near neutral basicity and provides high specificity for creatinine as compared with the chemical method. Therefore, the enzymatic method can overcome most disadvantages of the chemical method. However, the cost of reagents is high because enzymes used in the enzymatic method are very expensive and varied. Moreover, it is difficult to perform measurement without a special facility available for microdetermination.

In recent years, particularly diabetes (adult disease) has been increasing worldwide, which in turn increases not only diabetic nephropathy that is one of the complications of diabetes, but also severe kidney failure. As a remedy for these illnesses, e.g., dialysis or renal transplantation is needed. Thus, to prevent such nephropathy, particularly diabetic nephropathy at an early stage, a new measuring method has been demanded to determine creatinine as an indicator of kidney function in a safe, quick, and simple manner.

Therefore, with the foregoing in mind, it is an object of the present invention to provide a test piece for creatinine measurement.

A test piece for creatinine measurement of the present invention includes a compound expressed by the following formula (1).

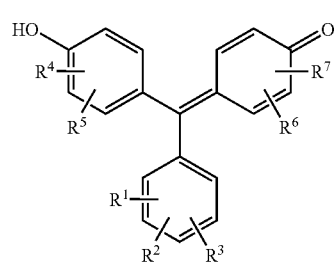

In the formula (1), $R^1$ represents H, $SO_3X$, or COOX. $R^4$ and $R^6$ represent OH, $SO_3X$, or COOX and may be either the same or different. $R^2$, $R^3$, $R^5$, and $R^7$ represent H, OH, Cl, Br, I, $NO_2$, NO, or $CH_3$ and may be either the same or different. Xs in the $R^1$, $R^4$, and $R^6$ represent H, Na, K, or $NH_4$ and may be either the same or different.

The present inventors developed a new method for measuring creatinine as follows. When creatinine was present while a complex-generating agent reacted with a metal to produce a colored complex, the creatinine competitively reacted with the metal to produce a complex and thus caused color fading of the colored complex. This color fading was used to measure the amount of creatinine. Consequently, the present inventors found for the first time that in the absence of creatinine, the compound expressed by the above formula reacted with a transition metal to produce a colored complex, and in the presence of creatinine, the creatinine inhibited formation of the colored complex and reacted with the transition metal to produce a non-colored complex. Therefore, when the test piece of the present invention including such a compound is used, e.g., to evaluate the presence or absence of a colored complex or the degree of formation of the colored complex, it can provide the degree of inhibition of the colored complex formation by creatinine. Thus, the amount of creatinine in a sample can be determined. Moreover, the test piece of the present invention allows a reaction to occur at room temperature. Therefore, unlike a conventional enzymatic method, it is not necessary to adjust the reaction temperature at an optimum temperature of the enzyme, so that the reaction time can be reduced. Accordingly, the creatinine measurement can be performed quickly and easily. Thus, the test piece of the present invention is useful particularly for measuring creatinine as an indicator of kidney function in the field of clinical care or the like.

BEST MODE FOR CARRYING OUT THE INVENTION

Figure 1:
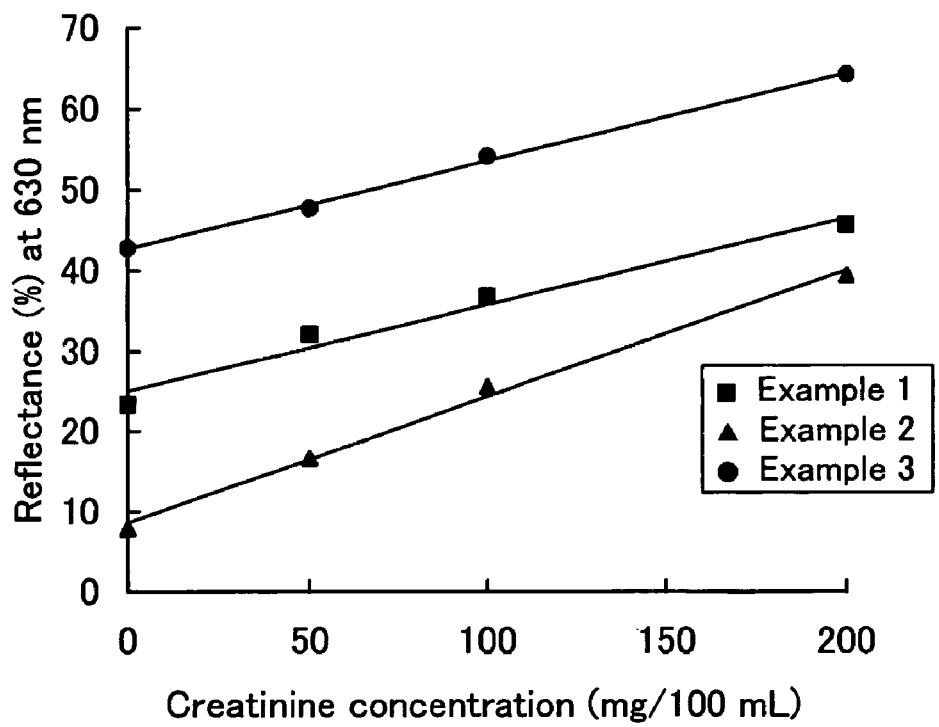
FIG. 1 is a graph showing the relationship between a creatinine concentration and reflectance in an example of the present invention.

A test piece for creatinine measurement of the present invention includes a compound expressed by the formula (1).

The compound may be expressed preferably by the following formula (2), more preferably by the following formula (3), and further preferably by the following formula (4). These compounds are water-soluble and can react easily, e.g., in measuring creatinine of a liquid sample or the like, so that the measurement can be performed with even higher sensitivity.

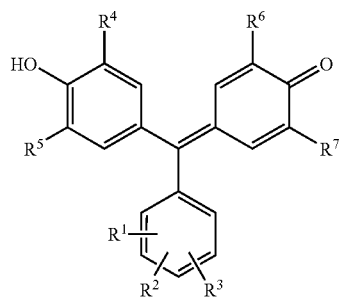

(2)

In the formula (2), $R^1$ represents H, $SO_3X$, or COOX. $R^4$ and $R^6$ represent OH, $SO_3X$, or COOX and may be either the same or different. $R^2$, $R^3$, $R^5$, and $R^7$ represent H, OH, Cl, Br, I, $NO_2$, NO, or $CH_3$ and may be either the same or different. Xs in the $R^1$, $R^4$, and $R^6$ represent H, Na, K, or $NH_4$ and may be either the same or different.

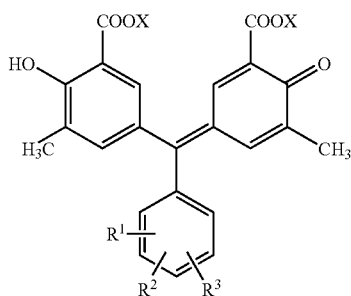

(3)

In the formula (3), $R^1$ represents H, $SO_3X$, or COOX. $R^2$ and $R^3$ represent H, OH, Cl, Br, I, $NO_2$, NO, or $CH_3$ and may be either the same or different. Xs represent H, Na, K, or $NH_4$ and may be either the same or different.

Among these compounds, compounds expressed by the following formulas (4) to (7) are preferred.

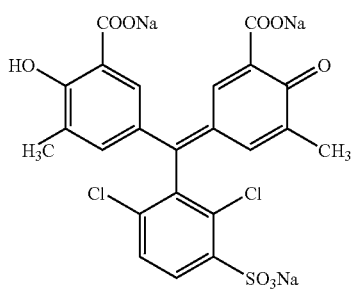

(4)

The compound of the formula (4) is 2,6-dichloro-4'-hydroxy-3',3"-dimethyl-3-sulfofuchsone-5',5"-dicarboxylic acid trisodium salt (referred to as "Chromazurol S" in the following). The compound of the formula (5) is 2,6-dichloro-4'-hydroxy-3',3"-dimethylfuchsone-5',5"-dicarboxylic acid disodium salt (referred to as "Chromazurol B" in the following). The compound of the formula (6) is chromoxane cyanine R (referred to as "Eriochrome Cyanine R" in the following). The compound of the formula (7) is pyrocatechol sulfonphthalein (referred to as "Pyrocatechol violet" in the following).

The method for producing each of the compounds is not particularly limited, and a conventionally known synthetic method may be employed. It is also possible to use commercially available products as the compounds. The Chromazurol S may be, e.g., Chrome Azurol S (produced by Nacalai Tesque, Inc.). The Chromazurol B may be, e.g., Chromazurol B (produced by DOJINDO LABORATORIES). The Eriochrome Cyanine R may be, e.g., Eriochrome Cyanine R (produced by Nacalai Tesque, Inc.). The Pyrocatechol violet may be, e.g., Pyrocatechol violet (produced by DOJINDO LABORATORIES).

In the test piece for creatinine measurement of the present invention, it is preferable that a porous material includes the above compounds.

Any type of porous material can be used, such as filter paper, a glass filter, or a resin porous film. Among these porous materials, the filter paper is preferred in view of cost, handling, or the like. Examples of a material for the resin porous film include polysulfone, polyester, nylon, nitrocellulose, and polycarbonate. The porous material may have an average pore size sufficient for the penetration and retention of a liquid sample, e.g., in the range of 3 to 10 μm.

It is preferable that the test piece for creatinine measurement of the present invention further includes a metal or its salt (also referred to as "metal" in the following) that forms a colored complex with the compound.

The metal may be, e.g., a transition metal or its salt. Examples of the transition metal include Cu(II), Pd(II), U(VI), Zr(IV), Ti(IV), Mn(II), Fe(III), Co(II), Ni(II), Mo(VI), and Sn(IV) or salt of any one of these metals. In particular, Cu(II) and Pd(II) are preferred, and Pd(II) is more preferred. The salts of these metals preferably have high water solubility, such as halide or sulfate.

A combination of the compound and the metal may be, e.g., Chromazurol S and Pd(II), Chromazurol B and Pd(II), Eriochrome Cyanine R and Cu(II), or Pyrocatechol violet and Cu(II). In particular, the combination of Chromazurol S and Pd(II) is preferred.

It is preferable that the test piece for creatinine measurement of the present invention further includes a buffer agent. Examples of the buffer agent include phosphate, borate, acetate, citrate, succinate, and trishydroxymethylaminomethane. In particular, phosphate, borate, and acetate are preferred, and phosphate is more preferred.

It is preferable that the test piece for creatinine measurement of the present invention further includes a surfactant to control the stability of a colored complex made of the compound expressed by the formula (1) and the metal. When the surfactant controls the stability of the colored complex, a competitive reaction of the metal with creatinine to produce a complex occurs more easily than a reaction of the metal with the compound to produce a colored complex in the presence of creatinine. This can improve the reactivity of the metal and creatinine, resulting in higher precision measurement of creatinine.

The surfactant is not particularly limited, and may be, e.g., a nonionic surfactant, anionic surfactant, or cationic surfactant. These surfactants can be used individually, or at least two of them may be used together.

Examples of the nonionic surfactant include polyvinyl alcohol (PVA), polyvinyl pyrrolidone (PVP), polypropylene glycol, polyethylene glycol, Triton series surfactant, Tween series surfactant, and Brij series surfactant. In particular, PVA, Triton-X100, and polyethylene glycol are preferred, and polyethylene glycol is more preferred.

Examples of the anionic surfactant include sodium dodecyl sulfate (SDS), sodium dodecylbenzenesulfonate, sodium cholate, and sodium deoxycholate. In particular, SDS and sodium cholate are preferred, and SDS is more preferred.

Examples of the cationic surfactant include benzyltrimethylammonium bromide, cetyltrimethylammonium bromide, benzalkonium chloride, and zephiramine. In particular, benzyltrimethylammonium bromide and cetyltrimethylammonium bromide are preferred, and benzyltrimethylammonium bromide is more preferred.

As described above, the surfactants can be used individually or in combinations of two or more. The combinations of the surfactants may be, e.g., the nonionic and anionic surfactants such as PVA and SDS, polyethylene glycol and sodium cholate, or Triton-X100 and SDS. Also, the combinations of the surfactants may be, e.g., the nonionic and cationic surfactants such as polyethylene glycol and benzyltrimethylammonium bromide or PVP and cetyltrimethylammonium.

The surfactant may affect the stability or color development of a colored complex made of the compound expressed by the formula (1) and the metal. Therefore, it is preferable that the surfactant is determined appropriately in accordance with the types of compound and metal.

Embodiment 1

The present invention will be described by showing an example of a test piece that includes the compound expressed by the formula (1), the metal and the buffer agent in the porous material.

The content of each reagent in the porous material is not particularly limited, and may be determined appropriately in accordance with the amount of sample or the like. Specifically, e.g., the compound may be in the range of $3 \times 10^{-3}$ to 1.5 μmol, and preferably 0.03 to 0.9 μmol, the metal may be in the range of $6 \times 10^{-3}$ to 0.9 μmol, and preferably 0.06 to 0.45 μmol, and the buffer agent may be in the range of 9 to 45 μmol, and preferably 12 to 30 μmol per cubic centimeter of the porous material. In this case, the volume of the sample added per cubic centimeter of the porous material generally ranges from 20 to 40 μl.

The compound (A) and the metal (B) may be present, e.g., at a ratio (molar ratio A:B) of 30:1 to 1:15, preferably 15:1 to 1:10, and further preferably 3:1 to 1:4. The compound (A) and the buffer agent (C) may be present, e.g., at a ratio (molar ratio A:C) of 1:10 to 1:1000, preferably 1:20 to 1:500, and further preferably 1:50 to 1:200.

When the surfactant further is used, it may be, e.g., in the range of 3 to 600 μg, and preferably 30 to 300 μg per volume of the porous material (1 $cm^3$). The compound (A) and the surfactant (D) may be present, e.g., at a ratio (molar ratio A:D) of 50:1 to 3:1, preferably 30:1 to 4:1, and further preferably 20:1 to 5:1.

The above test piece may be produced, e.g., by preparing a solution that includes the reagents, impregnating the porous material with the solution, and drying the porous material. The pH of the solution can be adjusted by the type of buffer agent or the like, and is preferably in the range of 5 to 9, and more preferably 6 to 8. Unlike a test piece that may include basic or acid substances, it is possible to prevent damage to the porous material because the solution is approximately neutral. This also can improve the stability of the test piece.

The concentration of each reagent in the solution may depend on, e.g., the amount of each reagent to be held in the porous material. Specifically, e.g., the compound may be in the range of 0.1 to 50 mmol/L, and preferably 1 to 30 mmol/L, the metal may be in the range of 0.2 to 30 mmol/L, and preferably 2 to 15 mmol/L, and the buffer agent may be in the range of 0.3 to 1.5 mol/L, and preferably 0.4 to 1 mol/L. When the surfactant further is used, it may be, e.g., in the range of 0.01 to 2 wt %, and preferably 0.1 to 1 wt %. Moreover, the amount of each reagent to be held in the porous material may be adjusted by repeating the impregnation of the porous material with the solution and the subsequent drying.

A solvent for the solution is not particularly limited, and water, a buffer solution, or the like can be used. Since the buffer agent is used as a reagent, a buffer solution including the buffer agent is suitable for the solvent. It is also preferable to use organic solvents such as ethanol, methanol, and acetone.

When the compound and the metal are mixed, they may react to produce a colored complex in the solution. However, even if the porous material is impregnated with such a solution, there is no problem in forming a complex of creatinine and the metal by the addition of a creatinine-containing sample. This is because even after the colored complex is formed, the creatinine is considered to have the ability to take the metal from the colored complex and produce a complex with this metal as well as inhibiting formation of the colored complex.

As described above, a colored complex of the compound and the metal in the solution does not affect the formation of a complex of creatinine and the metal. However, the formation of a colored complex may be suppressed beforehand in such a manner that a solution including the compound and a solution including the metal and the buffer agent are prepared separately, and the impregnation of a porous material and the subsequent drying are performed with each of the solutions. Specifically, e.g., the creatinine-measuring compound is dissolved in an organic solvent in which a metal is not dissolved easily, and the metal and the buffer agent are dissolved in water to prepare an aqueous solution. Then, the porous material is impregnated with the aqueous solution and is dried. This porous material further is impregnated with the creatinine-measuring compound solution of the organic solvent. Consequently, the compound and the metal can be held in the porous material without causing any reaction. The organic solvent in which the metal is not dissolved easily may be, e.g., acetone, toluene, or ethanol.

The porous material including the reagents also may be formed on a substrate because of ease of handling. In this case, any material can be used as the substrate, and a transparent resin or the like is preferred.

Next, an example of measuring the amount of creatinine in a liquid sample by using the test piece will be described.

First, the liquid sample is dropped on the test piece and allowed to react for a given time. The liquid sample penetrates the porous material, so that the compound and the metal in the porous material come into contact with each other to produce a colored complex. When the liquid sample includes creatinine, the creatinine inhibits formation of the colored complex. The amount of a colored complex formed in the porous film varies depending on the presence or absence of creatinine and its content in the liquid sample. Therefore, the degree of formation of the colored complex indicates the presence or absence of creatinine or the content of creatinine.

The reaction conditions are not particularly limited. For example, the reaction temperature is preferably in the range of 10 to 40° C., and more preferably 20 to 35° C. The reaction time is preferably in the range of 30 seconds to 5 minutes, and more preferably 1 to 3 minutes. When the reaction occurs at temperatures of not less than room temperature, it is preferable that the sample is left at room temperature before measurement.

After the reaction is completed, the degree of formation of the colored complex, i.e., the degree of inhibition of the colored complex formation by creatinine is determined. This can be performed, e.g., by optical measurement of the test piece. On the other hand, a creatinine standard solution with known concentration also can be measured optically using the test piece of the present invention. Then, a calibration curve plotting the measured values against the creatinine concentration is prepared. By substituting the measured values of the liquid sample in the calibration curve, the creatinine concentration of the sample can be determined.

The optical measurement of the test piece may include, e.g., measuring a reflectance or absorbance.

A measured wavelength of the reflectance or absorbance differs depending on the type of colored complex made of the compound and the metal. Therefore, the wavelength can be determined appropriately in accordance with, e.g., a combination of the compound and the metal. In the case of the combination of Chromazurol S and Pd(II), the combination of Chromazurol B and Pd(II), the combination of Eriochrome Cyanine R and Cu(II), or the combination of Pyrocatechol violet and Cu(II), the measured wavelength is preferably in the range of 560 to 700 nm, more preferably 600 to 670 nm, and further preferably 620 to 650 nm.

EXAMPLES

Next, examples will be described along with comparative examples.

Examples 1 to 3

Three mixtures (50 mL each) with the following compositions 1, 2, and 3 were prepared. A 0.34 mm thick filter paper ("Whatman 3MM Chr" produced by Whatman) was immersed in each of the mixtures. Then, the filter papers were dried at 50° C. for about 10 minutes, cut to 5 mm (length)×5 mm (width), and stuck on PET films by a double-sided adhesive tape, thus providing test pieces. These test pieces impregnated with the mixtures having the compositions 1, 2, and 3 were identified as examples 1, 2, and 3, respectively. As the compound, Eriochrome Cyanine R (produced by Nacalai Tesque, Inc.) of the formula (6), Chrome Azurol S (produced by of Nacalai Tesque, Inc.) of the formula (4), and Chromazurol B (produced by DOJINDO LABORATORIES) of the formula (5) were used.

| Composition 1 | |
| --- | --- |
| Boric acid buffer solution (pH 9.0) | 0.5 M |
| Copper (II) sulfate | 3.0 mM |
| Eriochrome Cyanine R | 6.0 mM |
| Composition 2 | |
| Citric acid buffer solution (pH 7.0) | 0.5 M |
| Palladium (II) chloride | 8 mM |
| Chromazurol S | 15 mM |
| Polyethylene glycol | 0.5 wt % |
| Composition 3 | |
| Boric acid buffer solution (pH 9.0) | 0.5 M |
| Copper (II) chloride | 3.0 mM |
| Chromazurol B | 3.0 mM |
| Polyethylene glycol | 0.1 wt % |

Measurement of Creatinine

A physiological saline solution and creatinine solutions (with 50 mg/100 mL, 100 mg/100 mL, and 200 mg/100 mL) obtained by dissolving creatinine (produced by Nacalai Tesque, Inc.) in a physiological saline solution were prepared as measurement samples. The test pieces of the examples 1, 2, and 3 were immersed in each of the measurement samples for about 2 seconds, then taken out of the samples, and left at room temperature for one minute. Subsequently, a reflectance (%) of the test pieces at 630 nm was measured by using a color-difference meter ("Σ90" produced by Murakami Color Research Laboratory). Table 1 and FIG. 1 show the results. FIG. 1 is a graph showing the correlation between the creatinine concentration and the reflectance.

TABLE 1

| Creatinine concentration | Reflectance (%) | | |
| --- | --- | --- | --- |
| | Example 1 | Example 2 | Example 3 |
| 0 mg/100 mL | 23.3 | 7.9 | 42.8 |
| 50 mg/100 mL | 32.0 | 16.6 | 47.7 |

TABLE 1-continued

| Creatinine concentration | Reflectance (%) | | |
| --- | --- | --- | --- |
| | Example 1 | Example 2 | Example 3 |
| 100 mg/100 mL | 36.7 | 25.5 | 54.1 |
| 200 mg/100 mL | 45.6 | 39.4 | 64.2 |

As shown in Table 1 and FIG. 1, a correlation formula of the creatinine concentration and the reflectance was expressed by "y=0.107x+25 (correlation coefficient r=0.986)" in the example 1, "y=0.157x+8.6 (correlation coefficient r=0.998)" in the example 2, and "y=0.108x+43 (correlation coefficient r=0.999)" in the example 3. The results confirmed that a favorable correlation was established between the creatinine concentration and the reflectance of the test pieces of the examples.

Example 4

20 urine specimens were prepared as measurement samples. First, a creatinine concentration was measured on each of the specimens by a Jaffe method using a quantitative reagent ("Creatinine-HA test Wako" produced by Wako Pure Chemical Industries, Ltd.) and a Hitachi 7070 automatic analyzer (produced by Hitachi, Ltd.). Next, the test piece of the example 2 was immersed in each of the measurement samples for about 2 seconds, then taken out of the samples, and left at room temperature for one minute. Subsequently, a reflectance (%) of the test pieces at 630 nm was measured by using a color-difference meter ("Σ90" produced by Murakami Color Research Laboratory).

Figure 2:
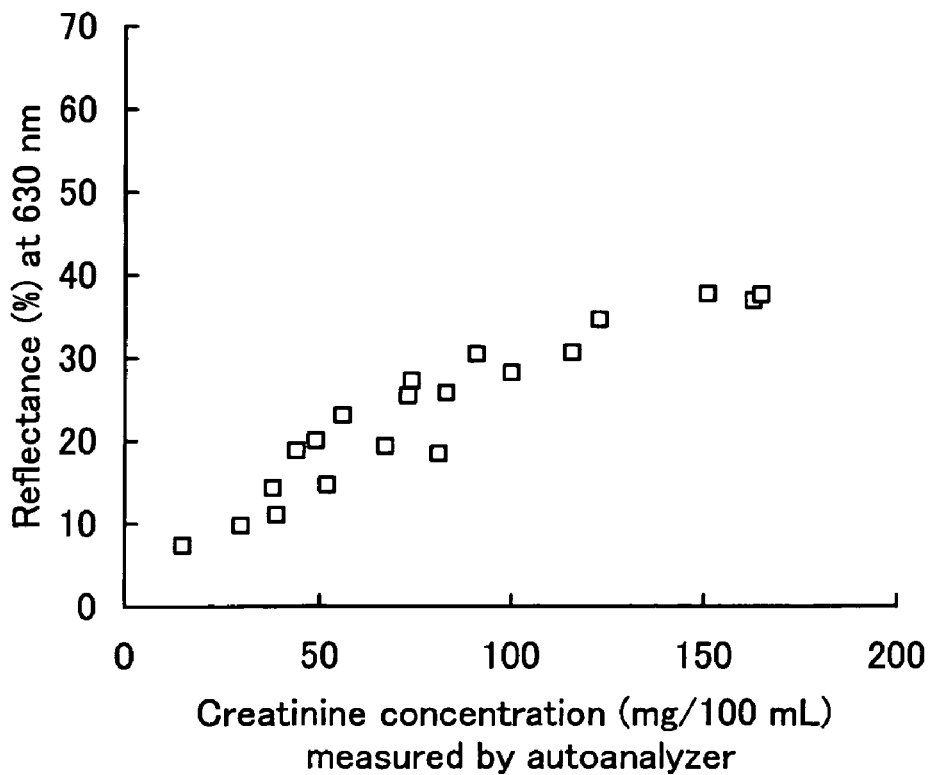
FIG. 2 is a graph showing the relationship between a creatinine concentration and reflectance in an example of the present invention.

Table 2 and FIG. 2 show the results of the creatinine concentration (measured by the Jaffe method) and the reflectance (measured using the test piece of the example 2) of each of the measurement samples. In FIG. 2, the x axis represents the creatinine concentration (mg/100 mL) of each sample that was measured by the automatic analyzer, and the y axis represents the reflectance (%) of each sample that was measured using the test piece of the example 2.

TABLE 2

| Specimen No. | Creatinine concentration (mg/100 mL) | Reflectance (%) |
| --- | --- | --- |
| 1 | 15 | 7.3 |
| 2 | 30 | 9.7 |
| 3 | 38 | 14.3 |
| 4 | 39 | 11.1 |
| 5 | 44 | 18.8 |
| 6 | 49 | 20.0 |
| 7 | 52 | 14.6 |
| 8 | 56 | 23.1 |
| 9 | 67 | 19.3 |
| 10 | 73 | 25.4 |
| 11 | 74 | 27.2 |
| 12 | 81 | 18.4 |
| 13 | 83 | 25.8 |
| 14 | 91 | 30.4 |
| 15 | 100 | 28.2 |
| 16 | 116 | 30.6 |
| 17 | 123 | 34.6 |
| 18 | 151 | 37.7 |
| 19 | 163 | 36.9 |
| 20 | 165 | 37.6 |

As shown in Table 2 and FIG. 2, the results confirmed that a favorable correlation was established between the creatinine concentration measured by the Jaffe method and the reflectance of the test piece of the example 2 in each of the measurement samples, which was expressed by a correlation formula of "y=0.201x+7.4 (correlation coefficient r=0.938)".

INDUSTRIAL APPLICABILITY

A test piece for creatinine measurement of the present invention is a novel test piece that includes the creatinine-measuring compound as described above. The test piece utilizes the inhibition of colored complex formation by creatinine and can determine the amount of creatinine easily. Therefore, the present invention is useful for the measurement of creatinine as an indicator of kidney function in clinical care or the like.

The invention claimed is:

1. A test piece for creatinine measurement comprising:
a compound expressed by the following formula (1)

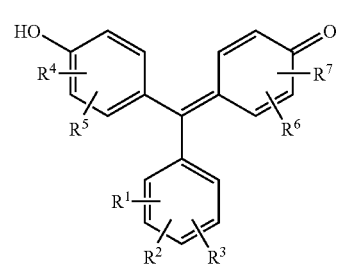

(1)

where $R^1$ represents H, $SO_3X$ or COOX,
$R^4$ and $R^6$ represent OH, $SO_3X$, or COOX and are either the same or different,
$R^2$, $R^3$, $R^5$ and $R^7$ represent H, OH, Cl, Br, I, $NO_2$, NO, or $CH_3$ and are either the same or different, and
Xs in the $R^1$, $R^4$ and $R^6$ represent H, Na, K, or $NH_4$ and are either the same or different, and
a transition metal or its salt that forms a colored complex with the compound,
wherein the transition metal is Pd(II), wherein the compound and the transition metal are included in a porous material.

2. The test piece for creatinine measurement according to claim 1, wherein the compound is expressed by the following formula (2)

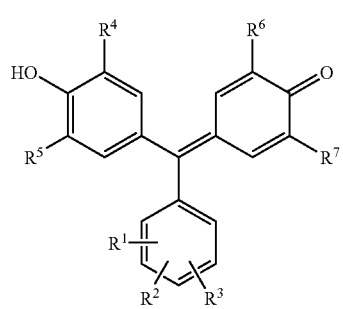

(2)

where $R^1$ represents H, $SO_3X$, or COOX,
$R^4$ and $R^6$ represent OH, $SO_3X$, or COOX and are either the same or different,
$R^2$, $R^3$, $R^5$ and $R^7$ represent H, OH, Cl, Br, I, $NO_2$, NO, or $CH_3$ and are either the same or different, and Xs in the $R^1$, $R^4$ and $R^6$ represent H, Na, K, or $NH_4$ and are either the same or different.

3. The test piece for creatinine measurement according to claim 2, wherein the compound is expressed by the following formula (3)

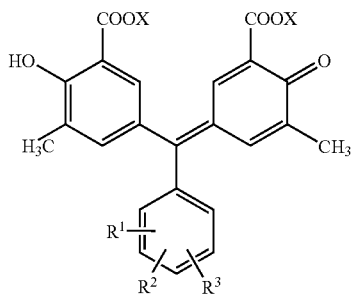

(3)

where $R^1$ represents H, $SO_3X$, or COOX,
$R^2$ and $R^3$ represent H, OH, Cl, Br, I, $NO_2$, NO, or $CH_3$ and are either the same or different, and
Xs represent H, Na, K, or $NH_4$ and are either the same or different.

4. The test piece for creatinine measurement according to claim 1, wherein the compound is expressed by the following formula (4)

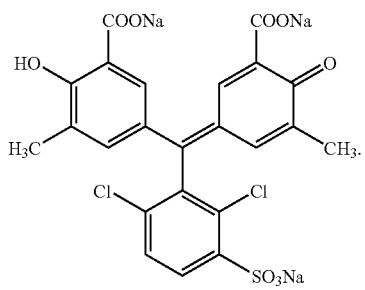

(4)

5. The test piece for creatinine measurement according to claim 1, wherein the compound is expressed by the following formula (5)

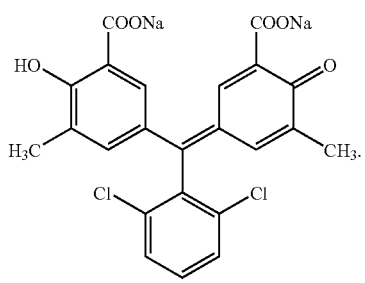

(5)

6. The test piece for creatinine measurement according to claim 1, wherein the compound is expressed by the following formula (6)

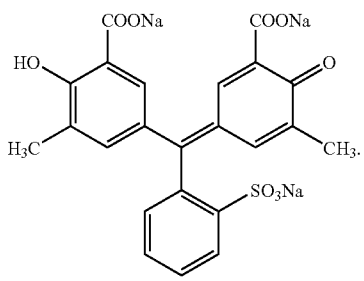

(6)

7. The test piece for creatinine measurement according to claim 1, wherein the compound is expressed by the following formula (7)

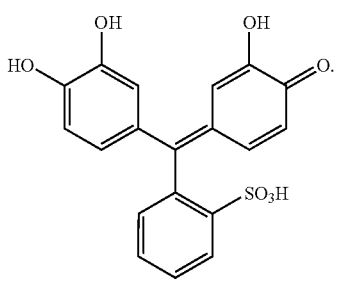

(7)

8. The test piece for creatinine measurement according to claim 1, wherein the compound (A) and the metal or its salt (B) are present at a ratio (molar ratio A:B) of 30:1 to 1:15.

9. The test piece for creatinine measurement according to claim 1, further comprising a buffer agent.

10. The test piece for creatinine measurement according to claim 9, wherein the compound (A) and the buffer agent (C) are present at a ratio (molar ratio A:C) of 1:10 to 1:1000.

11. The test piece for creatinine measurement according to claim 1, further comprising a surfactant.

12. The test piece for creatinine measurement according to claim 11, wherein the compound (A) and the surfactant (D) are present at a ratio (molar ratio A:D) of 50:1 to 3:1.

* * * * *